US010786226B2

(12) United States Patent
Pelissier et al.

(10) Patent No.: US 10,786,226 B2
(45) Date of Patent: Sep. 29, 2020

(54) ULTRASOUND SYSTEMS AND METHODS FOR OPTIMIZING MULTIPLE IMAGING PARAMETERS USING A SINGLE USER INTERFACE CONTROL

(71) Applicant: Clarius Mobile Health Corp., Burnaby (CA)

(72) Inventors: Laurent Pelissier, North Vancouver (CA); Trevor Stephen Hansen, Vancouver (CA); Benjamin Eric Kerby, Richmond (CA); Kris Dickie, Vancouver (CA); Nishant Uniyal, Vancouver (CA); Narges Afsham, Coquitlam (CA); David Glenn Willis, Woodinville, WA (US)

(73) Assignee: Clarius Mobile Health Corp., Burnaby, British Columbia (CA)

( * ) Notice: Subject to any disclaimer, the term of this patent is extended or adjusted under 35 U.S.C. 154(b) by 537 days.

(21) Appl. No.: 15/429,110

(22) Filed: Feb. 9, 2017

(65) Prior Publication Data
US 2018/0220995 A1 Aug. 9, 2018

(51) Int. Cl.
*A61B 8/00* (2006.01)
*A61B 8/08* (2006.01)
(52) U.S. Cl.
CPC ............ *A61B 8/467* (2013.01); *A61B 8/5207* (2013.01); *A61B 8/54* (2013.01); *A61B 8/565* (2013.01);
(Continued)
(58) Field of Classification Search
CPC combination set(s) only.
See application file for complete search history.

(56) References Cited

U.S. PATENT DOCUMENTS 5,241,349 A 8/1993 Nagasaka
5,482,045 A 1/1996 Rust et al.
(Continued)

FOREIGN PATENT DOCUMENTS

CA 3007936 8/2018
EP 0533976 B1 5/1996
(Continued)

OTHER PUBLICATIONS

Barr, R.G. and Grajo, J.R., "Dynamic Automatic Ultrasound Optimization: Time Savings, Keystroke Savings, and Image Quality", in Ultrasound Quarterly 25.2 (2009): 63-65.
(Continued)

*Primary Examiner* — Oommen Jacob
(74) *Attorney, Agent, or Firm* — Julian Ho

(57) ABSTRACT

The present embodiments relate generally to ultrasound imaging systems and methods that provide a user interface on the touchscreen display. The user interface includes an ultrasound image feed and a single control for modifying imaging depth of the ultrasound image feed. When input via the single control is received to modify the imaging depth, the system: adjusts frequency of ultrasound signals being used to acquire the ultrasound image feed; adjusts a beamformer parameter of the ultrasound signals being used to acquire the ultrasound image feed; receives first image data of the ultrasound image feed based on the adjusted frequency and the adjusted beamformer parameter; based on the first image data, adjusts Time Gain Compensation (TGC) of the ultrasound image feed; and receives second image data of the ultrasound image feed based on the adjusted frequency, beamformer parameter and TGC. Display of the second image data on the touchscreen display is then optimized without receipt of additional user input.

19 Claims, 7 Drawing Sheets

(52) U.S. Cl.
CPC ........... *A61B 8/4444* (2013.01); *A61B 8/4483* (2013.01); *A61B 8/461* (2013.01)

(56) References Cited

U.S. PATENT DOCUMENTS

| | | | |
|---|---|---|---|
| 6,063,030 A * | 5/2000 | Vara | G16H 40/63 |
| | | | 600/437 |
| 6,468,212 B1 * | 10/2002 | Scott | A61B 8/00 |
| | | | 600/437 |
| 6,743,174 B2 | 6/2004 | Ng et al. | |
| 7,833,159 B2 | 11/2010 | Ahn et al. | |
| 7,846,098 B2 | 12/2010 | Bakircioglu et al. | |
| 7,921,717 B2 * | 4/2011 | Jackson | G03B 42/06 |
| | | | 600/443 |
| 8,235,905 B2 | 8/2012 | Lin et al. | |
| 8,357,094 B2 | 1/2013 | Mo et al. | |
| 8,414,493 B2 * | 4/2013 | Derby, Jr. | A61B 8/00 |
| | | | 600/442 |
| 2007/0165925 A1 | 7/2007 | Ahn et al. | |
| 2008/0119731 A1 | 5/2008 | Becerra et al. | |
| 2009/0069682 A1 * | 3/2009 | Hastings | G01S 7/52084 |
| | | | 600/443 |
| 2010/0094132 A1 | 4/2010 | Hansen et al. | |
| 2010/0298701 A1 | 11/2010 | Shin | |
| 2011/0110576 A1 * | 5/2011 | Kreeger | G16H 50/50 |
| | | | 382/132 |
| 2013/0253323 A1 | 9/2013 | Kim | |
| 2014/0114190 A1 | 4/2014 | Chiang et al. | |
| 2014/0121524 A1 | 5/2014 | Chiang et al. | |
| 2015/0297179 A1 | 10/2015 | Mander et al. | |
| 2016/0081662 A1 | 3/2016 | Denk et al. | |
| 2017/0011252 A1 * | 1/2017 | Yang | A61B 8/54 |

FOREIGN PATENT DOCUMENTS

| | | | |
|---|---|---|---|
| EP | 2254033 A1 | 11/2010 | |
| FR | 2861192 A1 * | 4/2005 | ............ A61B 8/465 |
| WO | 9515521 A2 | 6/1995 | |
| WO | 2006040697 A1 | 4/2006 | |
| WO | 2008091950 A1 | 7/2008 | |
| WO | 2015136336 A1 | 9/2015 | |

OTHER PUBLICATIONS

Keebomed Inc. Ultra Compact & Ultra Light Chison ECO 1 Ultrasound—Introduction to Easy Diagnosis. Published on Nov. 11, 2014. Available at https://www.youtube.com/watch?v=6fp0hbIGkkw, last accessed Mar. 2, 2017.

Sonosite Iviz. Fujifilm SonoSite, Inc. Publication date unknown. Available at https://www.sonosite.com/product/sonosite-iviz , last accessed Mar. 2, 2017.

Hackett, G. X-Port Tutorial. Published on Apr. 2, 2015. Available at https://www.youtube.com/watch?v=_hIPxd7fb2Q), last accessed Mar. 2, 2017.

Heller, L.B. (2011). "Knobology for Image Optimization", in Society of Cardiovascular Anesthesiologists.

Notice of Allowance for corresponding Canadian Patent Application No. 3,007,936 filed Feb. 6, 2018.

International Search Report and Written Opinion of the International Searching Authority for corresponding PCT International Application No. PCT/CA2018/050133 filed Feb. 6, 2018.

* cited by examiner

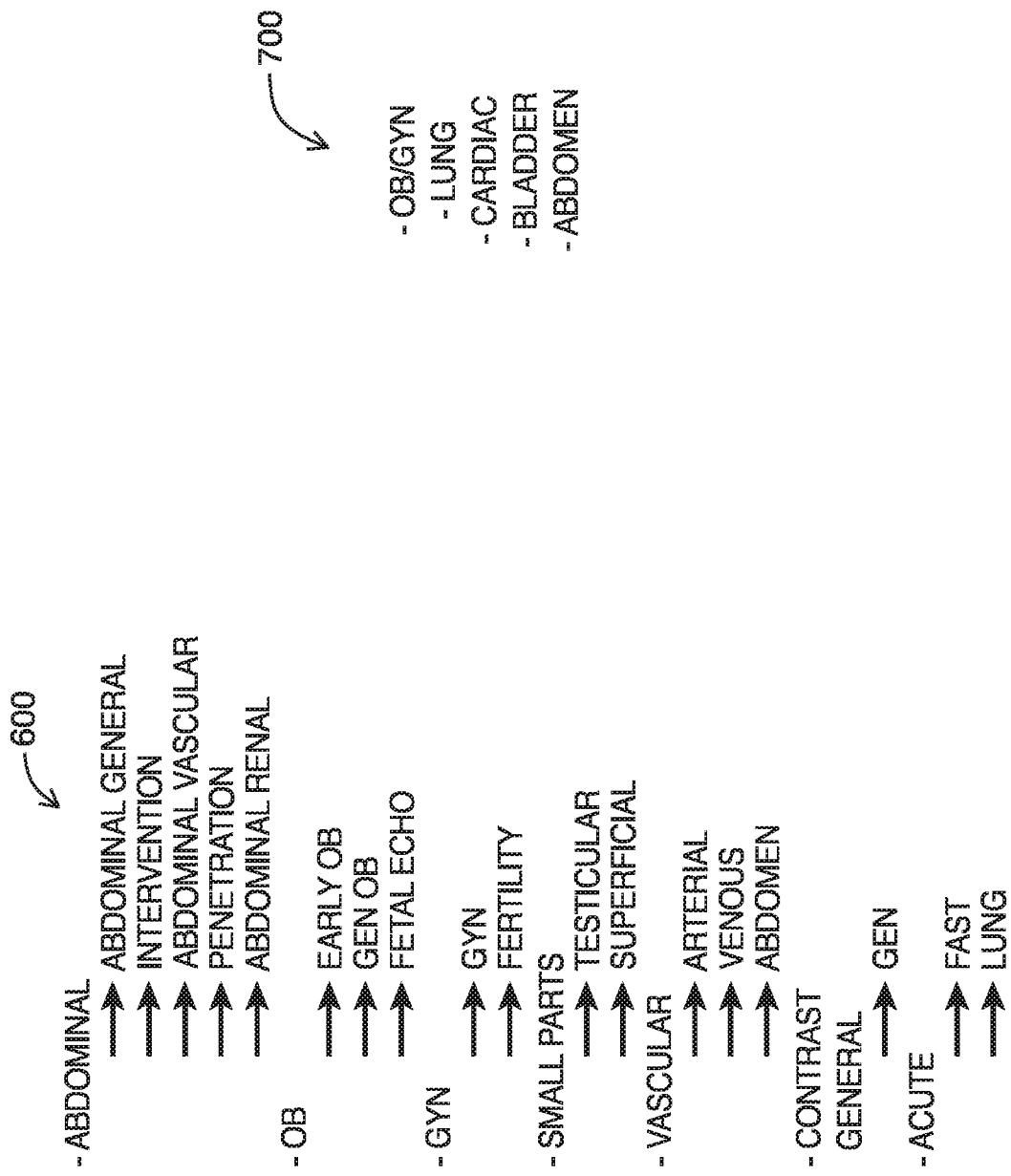

ULTRASOUND SYSTEMS AND METHODS FOR OPTIMIZING MULTIPLE IMAGING PARAMETERS USING A SINGLE USER INTERFACE CONTROL

FIELD

The present disclosure relates generally to ultrasound imaging, and in particular, user interface controls for modifying imaging parameters on ultrasound systems.

BACKGROUND

Ultrasound imaging systems are a powerful tool for performing real-time, non-invasive imaging procedures in a wide range of medical applications. An ultrasound machine includes a transducer which sends out ultrasound signals into tissue. Ultrasound waves are reflected back from the tissue and are received by the transducer. The reflected signals are processed to produce an ultrasound image of the target anatomy. An ultrasound machine typically has a user input device by which the operator of the ultrasound machine can control the machine to obtain images of tissue structures. Traditionally, the images may be displayed on a display incorporated in the ultrasound machine, and the user input device may include a keyboard.

A challenging part of acquiring ultrasound images is adjusting the various imaging parameters to optimize the image viewable. Conventional ultrasound systems have large physical control interfaces with numerous controls that allow modifying of various imaging parameters affecting the displayed image quality. It is typically required that multiple controls need to be manipulated to achieve an image with good quality. The manipulation of multiple controls to optimize image quality may not be intuitive, and users may require extensive training to learn the how the operation of these controls impact image quality.

There is an increasing demand for small portable ultrasound imaging devices that are easier to operate and that acquire good quality ultrasound images of the target anatomy. Small portable devices typically have smaller screens, and thus less room to display the many user interface controls traditionally appearing on an ultrasound user interface. On some existing ultrasound systems that provide ultrasound images on a touchscreen display, on-screen controls mimic the physical controls of a traditional ultrasound imaging system. These types of controls may obscure viewing of the ultrasound images being acquired.

There is thus a need for improved ultrasound systems and methods that optimize multiple imaging parameters using a single user interface control. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which:

FIG. 6 is an example preset tree of a traditional ultrasound imaging system;

FIG. 7 is an example list of presets in an ultrasound imaging system, in accordance with at least one embodiment of the present invention.

DETAILED DESCRIPTION

Figure 1:
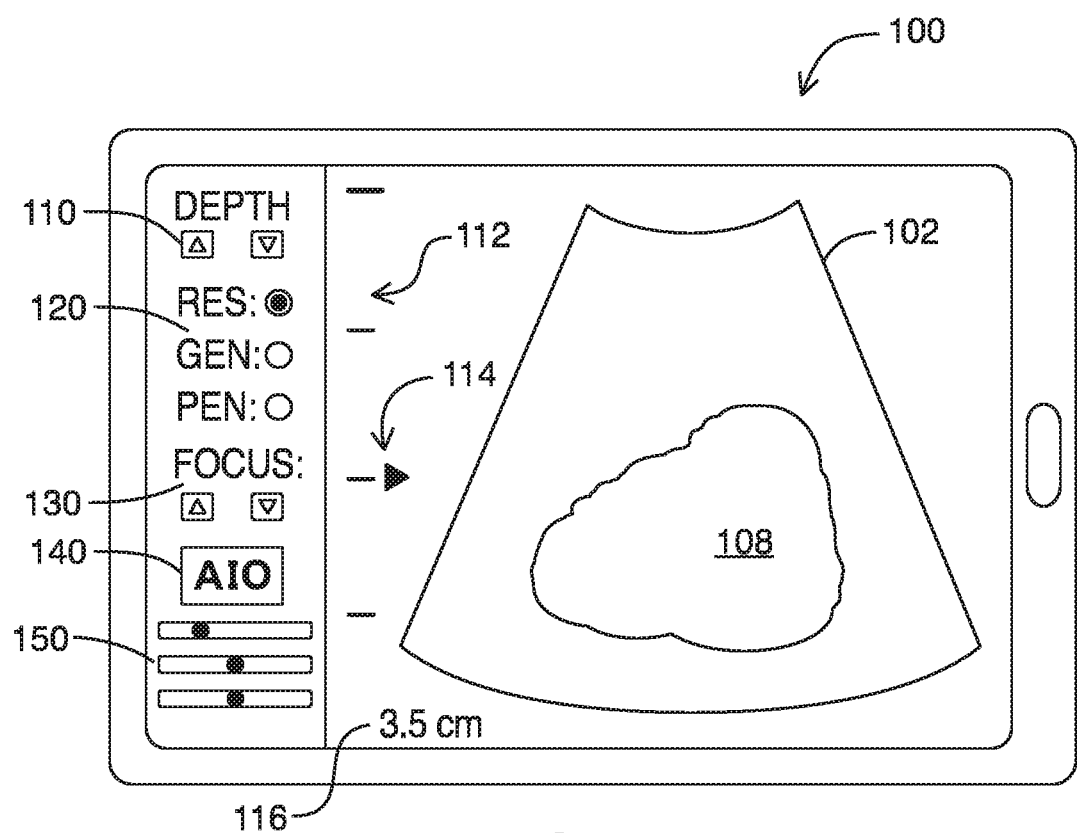
FIG. 1 shows an example user interface that may be provided on a display of a traditional touchscreen ultrasound system.

In a first broad aspect of the present disclosure, there is provided an ultrasound imaging system, including a touchscreen display; and a processor configured to execute instructions that cause the processor to provide a user interface on the touchscreen display, the user interface including an ultrasound image feed and a single control for modifying imaging depth of the ultrasound image feed. Upon receipt of input via the single control to modify the imaging depth of the ultrasound image feed, the processor causes the ultrasound imaging system to: adjust frequency of ultrasound signals being used to acquire the ultrasound image feed; adjust a beamformer parameter of the ultrasound signals being used to acquire the ultrasound image feed; receive first image data of the ultrasound image feed based on the adjusted frequency and the adjusted beamformer parameter; based on the first image data, adjust Time Gain Compensation (TGC) of the ultrasound image feed; and receive second image data of the ultrasound image feed based on the adjusted frequency, beamformer parameter and TGC; so that display of the second image data on the touchscreen display is optimized without receipt of additional user input.

In some embodiments, the input for the single control is receivable via a touch gesture on the touchscreen display. In some embodiments, the touch gesture includes a drag gesture.

In some embodiments, the user interface is substantially free of graphical controls for modifying non-depth imaging parameters of the ultrasound image feed. In some embodiments, these graphical controls include a graphical control for modifying any one of: frequency, focus position, number of focal zones, and TGC.

In some embodiments, the beamformer parameter is selected from the group consisting of: focus position, number of focal zones, receive filter frequency, and receive sampling frequency.

In some embodiments, the TGC of the ultrasound image feed is continuously adjusted after receiving the second image data, so that display of subsequent image data from the ultrasound image feed is optimized without receipt of additional user input.

In some embodiments, adjusting the TGC of the ultrasound image feed includes determining TGC offsets across multiple imaging depths of the first image data. In some embodiments, the TGC offsets are for achieving a predetermined target image intensity across the multiple imaging depths.

In another broad aspect of the present disclosure, there is provided a method of controlling viewing of an ultrasound image feed, the method including: providing a user interface on a touchscreen display, the user interface including an ultrasound image feed and a single control for modifying imaging depth of the ultrasound image feed; receiving input via the single control to modify the imaging depth of the ultrasound image feed; upon receipt of the input, adjusting frequency of ultrasound signals being used to acquire the ultrasound image feed, adjusting a beamformer parameter of the ultrasound signals being used to acquire the ultrasound image feed, receiving first image data of the ultrasound image feed based on the adjusted frequency and the adjusted beamformer parameter, based on the first image data, adjusting Time Gain Compensation (TGC) of the ultrasound image feed, and receiving second image data of the ultrasound image feed based on the adjusted frequency, beamformer parameter and TGC; so that display of the second image data on the touchscreen display is optimized without receipt of additional user input.

In some embodiments, the input for the single control is received via a touch gesture on the touchscreen display. In some embodiments, the touch gesture includes a drag gesture.

In some embodiments, the user interface is substantially free of graphical controls for modifying non-depth imaging parameters of the ultrasound image feed. In some embodiments, the graphical controls include a graphical control for modifying any one of: frequency, focus position, number of focal zones, and TGC.

In some embodiments, the beamformer parameter is selected from the group consisting of: focus position, number of focal zones, receive filter frequency, and receive sampling frequency.

In some embodiments, TGC of the ultrasound image feed is continuously adjusted after receiving the second image data, so that display of subsequent image data from the ultrasound image feed is optimized without receipt of additional user input.

In some embodiments, adjusting the TGC of the ultrasound image feed includes determining TGC offsets across multiple imaging depths of the first image data. In some embodiments, the TGC offsets are for achieving a predetermined target image intensity across the multiple imaging depths.

In another broad aspect of the present disclosure, there is provided a computer readable medium storing instructions for execution by a processor of a display unit for an ultrasound imaging system, the display unit having a touchscreen display, wherein when the instructions are executed by the processor, the display unit is configured to: provide a user interface on the touchscreen display, the user interface including an ultrasound image feed and a single control for modifying imaging depth of the ultrasound image feed; and receive input via the single control to modify the imaging depth of the ultrasound image feed. Upon receipt of the input, the processor causes the ultrasound imaging system to: adjust frequency of ultrasound signals being used to acquire the ultrasound image feed; adjust a beamformer parameter of the ultrasound signals being used to acquire the ultrasound image feed; receive first image data of the ultrasound image feed based on the adjusted frequency and the adjusted beamformer parameter; based on the first image data, adjust Time Gain Compensation (TGC) of the ultrasound image feed; and receive second image data of the ultrasound image feed based on the adjusted frequency, beamformer parameter and TGC; so that display of the second image data on the touchscreen display is optimized without receipt of additional user input.

In some embodiments, the user interface is substantially free of graphical controls for modifying non-depth imaging parameters of the ultrasound image feed.

For simplicity and clarity of illustration, where considered appropriate, reference numerals may be repeated among the figures to indicate corresponding or analogous elements or steps. Various ultrasound images are shown in the drawings are not drawn to scale, and are provided for illustrative purposes in conjunction with the description. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is an example user interface that may be provided on a display of a traditional touchscreen ultrasound system. The user interface may display an ultrasound image feed 102 in which a given anatomical structure 108 is viewable. The user interface may have elements that show the imaging depth such as a scale 112 and depth indicator 116. The user interface may also have a focus position indicator 114.

As noted, traditional ultrasound system 100 may provide virtual controls that mimic the operation of various physical controls available on conventional ultrasound systems. Some virtual controls that allow for optimizing of image quality are shown in FIG. 1. These virtual controls may include controls for modifying the imaging depth 110 (e.g., with virtual arrow buttons for increasing and decreasing imaging depth), the focus position of the ultrasound signals 130 (with virtual arrow buttons for raising or lowering the focus position), frequency of the ultrasound signals 120, and Time Gain Compensation (TGC) 150. There may also be a button for performing Automatic Image Optimization (AIO) 140, which may be selected to perform some automated image optimization with respect to the gain and overall contrast of the displayed image.

As will be understood by persons skilled in the art, the frequency controls 120 are shown in a typical manner where the user is presented with the option to select from 3 different frequencies of the range of possible frequencies available on a transducer: resolution ('RES') providing the highest frequency and lowest penetration, penetration ('PEN') providing the lowest frequency and highest penetration, and general ('GEN') providing mid-range frequencies that balance resolution with penetration. Similarly, the TGC controls 150 are provided in a typical manner as a set of sliders that adjust gain in specific areas of the image (near-, mid-, and far-field) to compensate for the effects of ultrasound signal attenuation.

Figure 2:
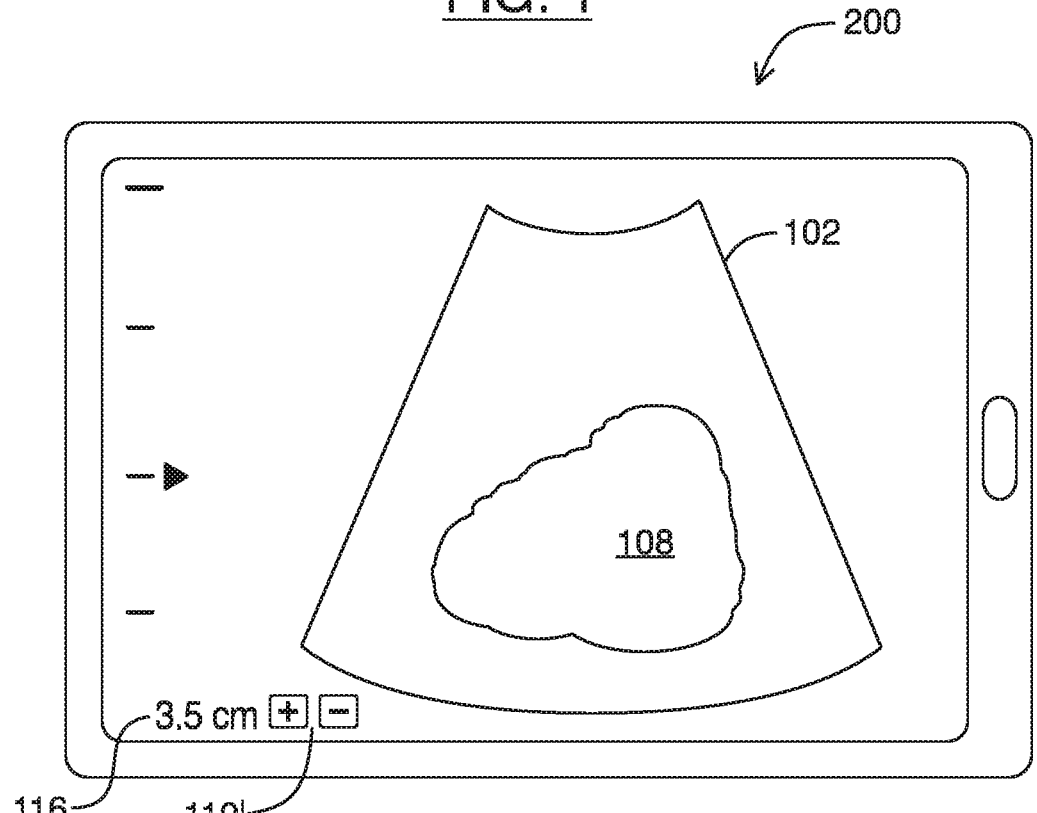
FIG. 2 shows an example user interface of an ultrasound system that receives input via a single control, in accordance with at least one embodiment of the present invention.

Referring to FIG. 2, shown there generally as 200 is an example user interface of an ultrasound system that receives input via a single control, in accordance with at least one embodiment of the present invention. As shown, the single control 110' modifies the imaging depth of the ultrasound image feed 102. As the 'up' and 'down' buttons are used, the imaging depth may increase or decrease correspondingly and the depth indicator 116 can be updated accordingly. Whereas traditional ultrasound systems require users to adjust a number of controls to optimize images being displayed, the use of a single control in the ultrasound system of the present embodiments may enhance user efficiency and ease-of-use. Also, the user interface in the present embodiments can be substantially free of graphical controls for modifying non-depth imaging parameters of the ultrasound image feed 102. This may provide more screen space to display the ultrasound image feed 102 and anatomical structures 108. As discussed below in relation to FIG. 4, the present embodiments can automatically adjust a number of imaging parameters based solely on the inputted imaging depth, to optimize the displayed image without additional user input.

Referring to FIGS. 3A-3D, shown there generally as 300-303 are a sequence of user interface interactions for receiving input to optimize image quality in the traditional user interface of FIG. 1. FIGS. 3A-3D show an example sequence of user interface control inputs that may be required to allow a user to view an anatomical feature that is deeper into the tissue than the view that is provided in FIG. 1.

Referring again to FIG. 1, it can be seen from the shape of the ultrasound image feed 102 that the ultrasound images are generated from a curvilinear transducer typically used for imaging into the abdomen. As noted above, the transducer may emit ultrasound signals at a range of frequencies. As shown, the anatomical feature 108 is roughly between '1-4 cm' deep into the tissue (as is shown by the depth indicator 116). Since this is relatively shallow for a curvilinear transducer, the frequency control 120 may be set to the 'RES' setting so that imaging is performed at the higher frequencies the transducer is capable of. Also, the focus position may be set to be roughly near the middle of the anatomical structure 108 at roughly '2 cm' deep, so that the anatomical structure 108 can be viewed clearly.

To image deeper into the tissue, a user may traditionally use the on-screen controls in a manner shown in FIGS. 3A-3D. Shown generally as 300 in FIG. 3A, the user may first use the imaging depth controls 110 (e.g., button '312' shown in bolded outline) to increase the imaging depth of the ultrasound image feed 102. This may result in the imaging depth of the ultrasound image feed 102 being increased to '10 cm' (as shown on the depth indicator 116 in FIG. 3A). In this view, the anatomical feature 108 remains viewable. However, because the frequency of the ultrasound signals being used to generate the ultrasound image feed 102 remains at the high-frequency 'RES' setting, the ultrasound signals may not penetrate deep enough into the tissue to allow for anatomical structures in the far field 310 to be discerned. This may result in the far field 310 of the ultrasound image feed 102 appearing dark (as shown with cross-hatch shading in FIG. 3A).

Figure 3A:
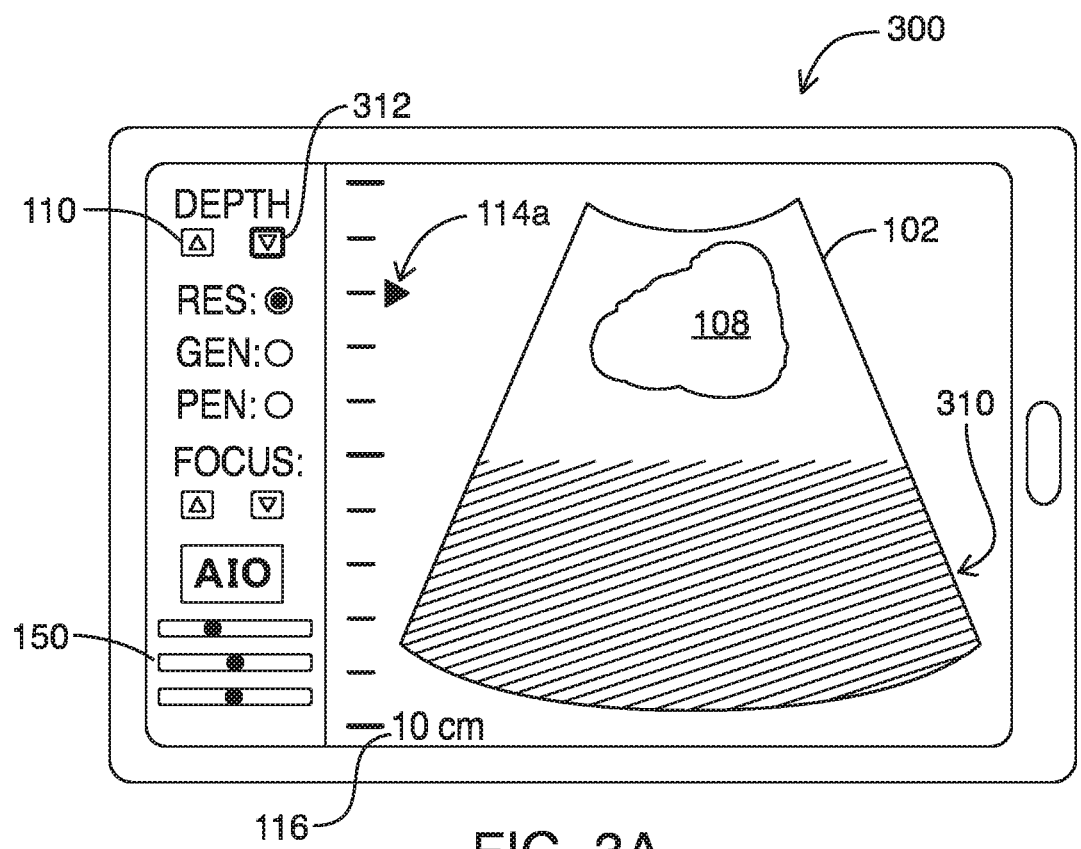
FIGS. 3A-3D are a sequence of user interface interactions for receiving input to optimize image quality in the traditional touchscreen ultrasound system of FIG. 1.
Figure 3B:
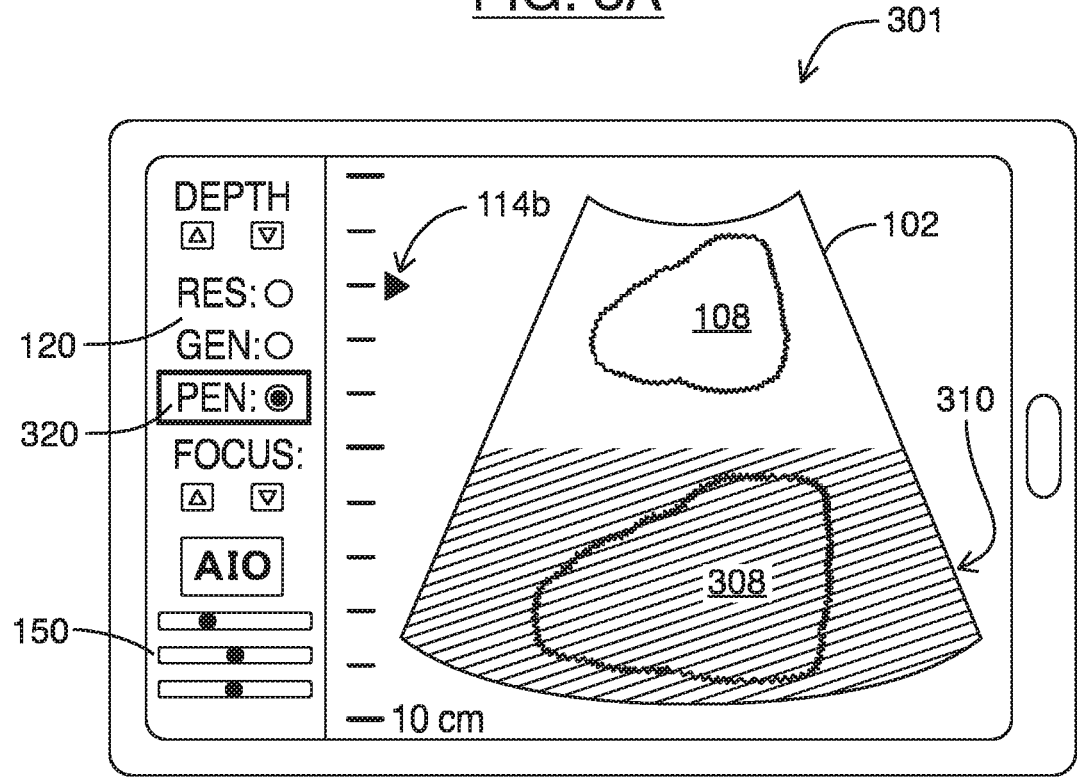

To increase the penetration of the ultrasound signals being used to image at the increased imaging depth of '10 cm', a user may next use the frequency controls 120 to decrease the frequency of the ultrasound signals being used to acquire ultrasound image feed 102. For example, shown generally as 301 in FIG. 3B, the user may activate the frequency controls 120 to select to the lower-frequency 'PEN' mode (shown as highlighted with bolded box 320 in FIG. 3B). This may result in the lower-frequency signals penetrating deeper into the tissue being imaged so as to be able to generate corresponding echoes that allow deeper tissues to be discerned and imaged in the ultrasound image feed 102. In the example illustration of FIG. 3B, it can be seen that although the far field 310 of the ultrasound image feed 102 may remain dark (still shown with cross-hatch shading), the use of the 'PEN' mode frequencies may allow for deeper penetration so as to allow another anatomical structure 308 to be viewable. As will be understood by persons skilled in the art, the use of the lower frequency 'PEN' mode 320 allows for deeper penetration at the expense of resolution. Accordingly, FIG. 3B also show the border lines of the anatomical structures 108, 308 becoming less well-defined. This is shown in FIG. 3B by the anatomical features 108, 308 being illustrated with jagged lines.

Figure 3C:
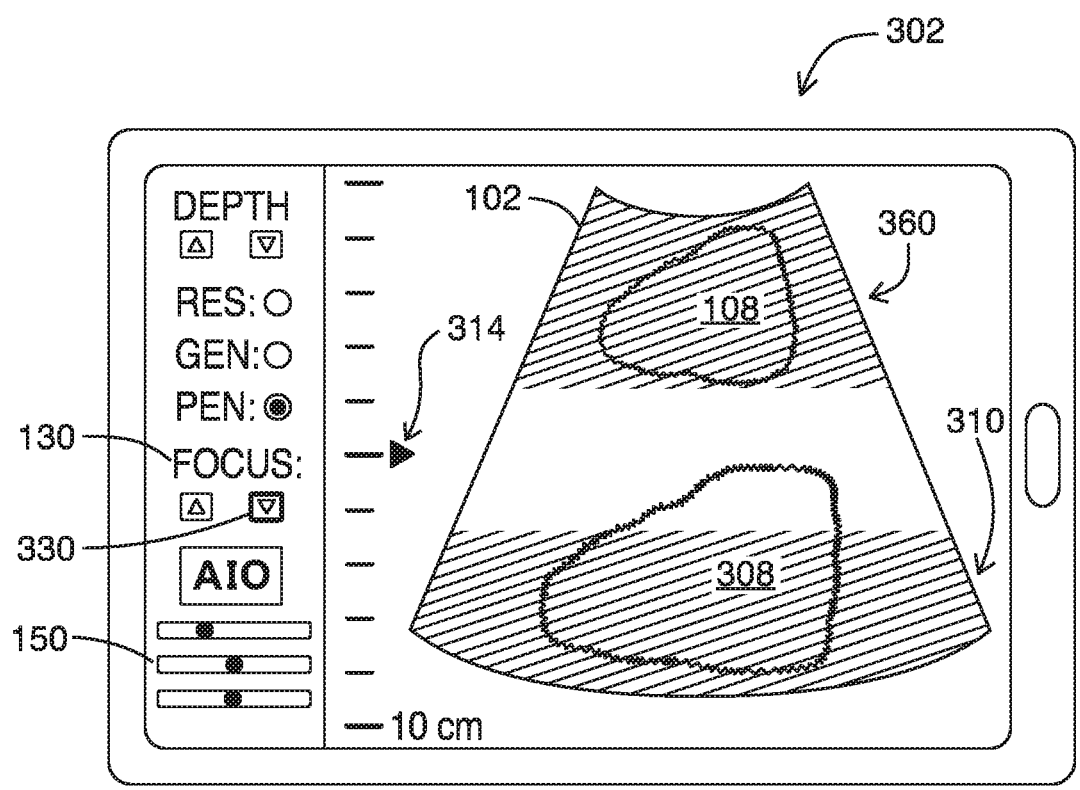

A next step that a user may take to improve the quality of the image being viewed can be to change the focus position of the ultrasound signals being used to acquire images for the ultrasound image feed 102. In FIGS. 3A and 3B, the focus position did not change from what was shown in FIG. 1 and remained at '2 cm' (as shown via the focus position indicator 114a, 114b). Referring now to FIG. 3C, shown there generally as 302 is how traditional on-screen controls on a touchscreen may next be used to lower the focus position deeper into the tissue. As shown, the focus position controls 130 may be used and a 'down' arrow button 330 (shown in bolded outline) may be selected to lower the focus position to around '5 cm' (as indicated by the new position of the focus position indicator 314). The lowering of the focus position may generally result in the portion of the image where the focus is moved to becoming brighter, so that the near field 360 of the image appears relatively darker (shown in FIG. 3C with cross-hatch shading). Also, the far field 310 of the image may remain dark (also shown in FIG. 3C with cross-hatch shading).

Figure 3D:
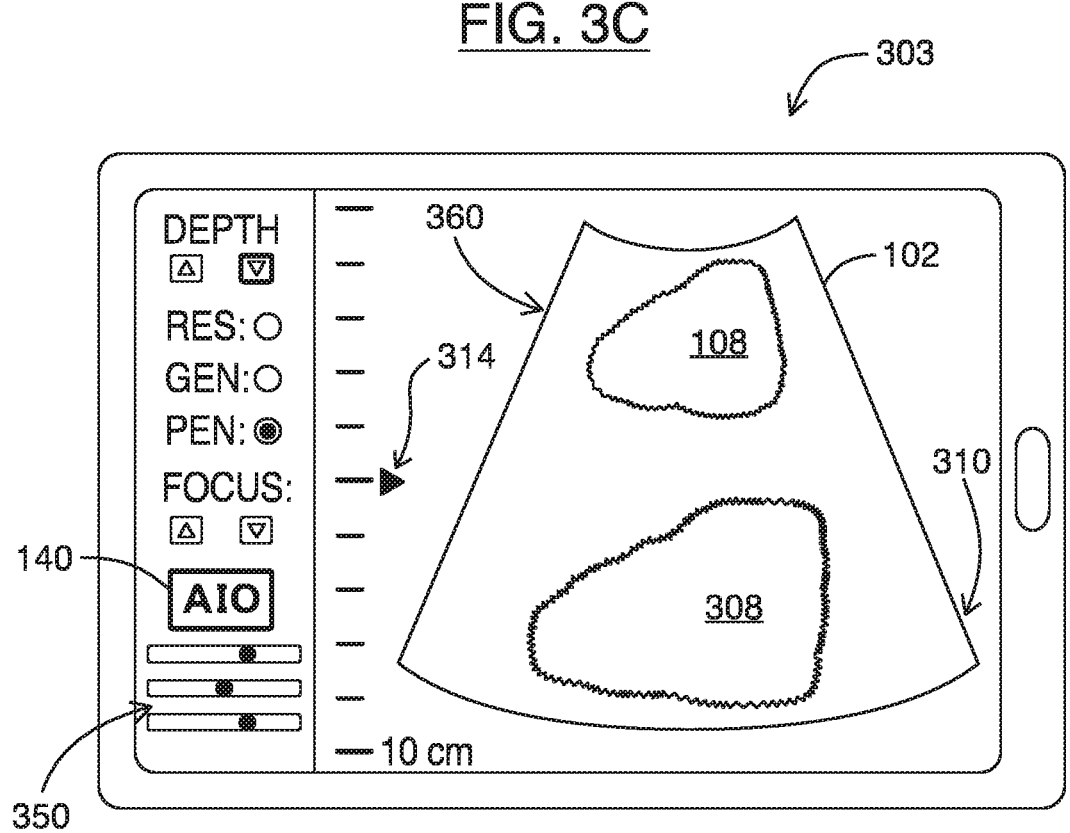

Since the ultrasound image being shown in FIG. 3C is still not showing the various anatomical features 108, 308 with sufficient brightness throughout the various imaging depths, a next step that the user may take is to perform an AIO operation. Referring to FIG. 3D, shown there generally as 303 is a further user interface subsequent to the one shown in FIG. 3C. As shown, the AIO button 140 (shown in bolded outline in FIG. 3D) may be selected to optimize the gain and overall contrast of the displayed image. For example, this may involve automatically adjusting the TGC controls 350.

As will be understood by persons skilled in the art, TGC is provided by increasing gain with depth in a stepwise manner according to a number of depth zones (e.g., near-, mid-, and far-fields). A default gain increase is applied in each depth zone (based on the expected average loss in the zone) in an attempt to provide a uniform background level throughout the field of view. Traditionally, the slider TGC controls then allow for manual adjustment of the default gain applied in each zone (either to reduce the gain applied or further enhance it).

Referring back to FIG. 1 where the imaging depth was '3.5 cm', it can be seen that the TGC controls (shown as a set of sliders arranged in a column for adjusting near-, mid-, and far-field gain from top to bottom) were set in a manner where no adjustments were made to the gain sliders in the mid-field and the far-field (the sliders remained in their respective middle positions). However, the gain was slightly reduced in the near-field (the slider is positioned slightly to the left of the middle position) where the image may have been too bright.

Referring now to FIGS. 3A-3C, it can be seen that as various other imaging parameter controls 110, 120, 130 were being adjusted, the TGC controls 150 remained unmodified. Referring simultaneously to FIG. 3D, the activation of the AIO button 140 may result in the TGC controls being modified so that they appear in the manner shown in control 350. Particularly, the slider for the far-field has been increased from the default gain setting to brighten the far field 310 of the ultrasound image feed 102 (which appeared dark in FIG. 3C). Similarly, the slider for the near-field has been increased from the previous less-than-default setting to brighten the near field 360 of the ultrasound image feed (which also appeared dark in FIG. 3C). As a result of the automatic gain adjustments made by activation of the AIO button 140 (as reflected in the TGC controls 350), the image in the ultrasound image feed 102 may show substantially uniform brightness throughout the imaging depths, so as to allow both the anatomical features 108, 308 within the field of view to be displayed more clearly.

As can be seen by FIGS. 3A-3D, traditional systems typically require input via a number of different virtual controls to modify various of the imaging parameters before an optimized image can be displayed. As discussed below, the present embodiments may allow input to be received via a single user interface control without the complexity and time typically required for user interface control input by traditional systems.

Figure 4:
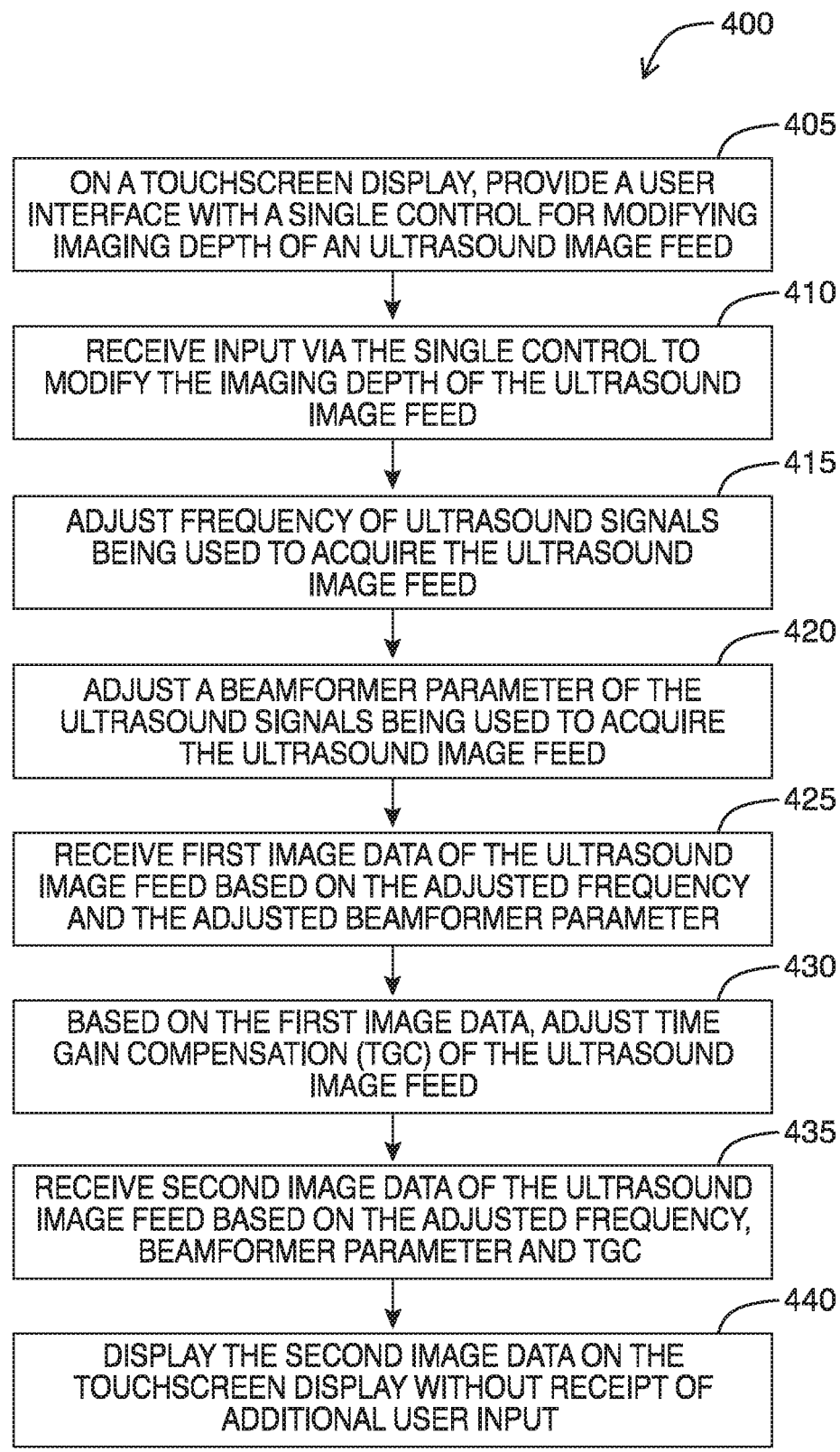
FIG. 4 is a flowchart diagram for steps of a method for optimizing multiple imaging parameters using a single user control in accordance with at least one embodiment of the present invention.

Referring to FIG. 4, shown there generally as 400 is a flowchart diagram for steps of a method for optimizing multiple imaging parameters using a single user control in accordance with at least one embodiment of the present invention. The method may also be considered a method for controlling viewing of an ultrasound image feed. The method may be performed by a computing device having a touchscreen display configured to communicate with an ultrasound transducer and display ultrasound images, such the display unit discussed in relation to FIG. 8. In discussing the method of FIG. 4, reference will simultaneously be made to the example user interfaces shown in FIGS. 2 and 5.

At 405, the touchscreen display may provide a user interface with a single control for modifying imaging depth of an ultrasound image feed. For example, ultrasound signal data may be generated from scanning tissue and the resultant live image feed being displayed on a touchscreen interface such as is shown in FIG. 2. As noted above, FIG. 2 shows an example embodiment of a user interface of an ultrasound system that receives input via a single control. Referring simultaneously to FIG. 2, it can be seen the user interface of the ultrasound system has a single control 110' (the '+' and '−' buttons) for adjusting imaging depth of the ultrasound image feed 102. Also shown in FIG. 2 (and FIG. 5) is a focus indicator similar to 114 in FIG. 1. However, in various embodiments, the focus indicator may be omitted to further enhance simplicity of the user interface.

At 410, the method may include receiving input via the single control to modify the imaging depth of the ultrasound image feed 102. In relation to the example shown in FIG. 2, the input may involve pressing of the '+' button in the imaging depth controls 110' to increase the imaging depth of the ultrasound image feed 102. As illustrated in FIG. 2, the depth control input is provided via '+' and '−' buttons 110; however, in various embodiments, the single control may be provided in any form.

For example, in some embodiments, the depth control input may be provided in the form of a touch gesture (e.g., a drag gesture) as is described in U.S. patent application Ser. No. 15/336,775 entitled "Systems and Methods for Controlling Visualization of Ultrasound Image Data", the entire contents of which are incorporated herein by reference. Other gestures for inputting the depth change may also be possible. In some embodiments, a camera on the display may be configured to recognize gestures to increase or decrease depth. Additionally or alternatively, the gyroscope and/or accelerometer may be configured to sense motion on the display device and translate such motion gesture (e.g., a twist or tilt gesture) as an input to increase or decrease imaging depth.

Upon receipt of input via the single control, acts 415 to 435 may be performed prior to an optimized ultrasound image feed 102 having the increased imaging depth is displayed.

Act 415 involves adjusting frequency of ultrasound signals being used to acquire the ultrasound image feed 102. As noted, higher frequency ultrasound signals provide higher resolution, but they are unable to penetrate as deep into tissue as lower frequency ultrasound signals. As such, modification of the ultrasound signal frequency may be performed in accordance with the ultrasound frequencies available on the transducer and the imaging depth that is desired. For example, if the input via the single control is to increase imaging depth, the frequency of the ultrasound signals may be decreased to enhance penetration. Conversely, if the input via the single control is to decrease imaging depth, less penetration may be required so the frequency of the ultrasound signals may be increased so as to take advantage of increased resolution provided by the higher frequency signals.

Act 420 involves adjusting a beamformer parameter of the ultrasound signals being used to acquire the ultrasound image feed 102. As will be understood by persons skilled in the art, transducers are typically made up of an array of small elements that can be selectively excited to generate ultrasound waves. Since the waves generated by these individual small elements will constructively interfere with each other when pulsed, the timing and sequence in which the elements are selected to be pulsed may allow a beam to be formed during a transmit function. Corresponding sum and delay operations can then be taken into account during reception to form one or more lines in a generated ultrasound image.

One example of a beamformer parameter that can be adjusted at act 420 is the focus position of the ultrasound signals being emitted. The transmit ultrasound signals may be focused at particular imaging depth to obtain better images of tissues at that depth. For example, as noted above with respect to FIG. 3C, doing so may traditionally cause the resultant ultrasound image to display a brighter band where the focus position is.

Another example of a beamformer parameter that may additionally or alternatively be adjusted is the number of focal zones. Although not discussed above with regards to the sequence of user interface interactions in FIGS. 3A-3D, another manual user interface interaction that may be inputted in traditional systems is to increase the number of focal zones. As will be understood by persons skilled in the art, modifying the focus position of the imaging depth may improve imaging of tissues at the depth where the signals are focused. However, the tissues at the depths where the ultrasound signals are not focused may lack clarity. To improve imaging across multiple depths, it is possible to add one or more focal zones when acquiring a single image frame, so that multiple ultrasound signals focused at different respective depths are projected and received. The image data from the multiple ultrasound signals are then combined into a single image frame that has improved imaging clarity at the different depths.

The trade-off for adding focal zones is a reduced frame rate due to additional transmit/receive events being required to generate a single image frame. However, the reduced frame rate may be acceptable in some instances because the perceived impact of the reduced frame rate may differ depending on the imaging depth. For example, at deep imaging depths (e.g., 8-30 cm), ultrasound signals are required to traverse a greater distance so multiple transmit/receive events may take a longer time to complete than if the transmit/receive events were implemented at shallower imaging depths (e.g., 1-6 cm, where the ultrasound signals need to only traverse a shorter distance and a frame with multiple focal zones can be generated more quickly). This allows the reduced frame rate resulting from adding focal zones to not be as severe when imaging in shallower depths, versus when imaging at deeper depths.

At act 420, in some embodiments, the number of focal zones may be increased or decreased as the imaging depth changes in view of the above factors. In one embodiment (e.g., when imaging using a linear transducer that operates at higher frequencies for imaging more superficial structures), the number of focal zones may be increased as imaging depth is increased to enhance image clarity across multiple imaging depths. The increased time to acquire image frames may be acceptable in this instance because imaging is being performed at relatively shallow depths (e.g., less than 6 cm), such that the lower frame rate may not be so severe for a user.

In another embodiment (e.g., when imaging using a curvilinear transducer that operates at lower frequencies for imaging tissues deeper into the body), the number of focal zones may be decreased as imaging depth is increased so as to preserve a desired frame rate. In this instance, at the shallower imaging depths for the curvilinear transducer, it may be desirable to use multiple focal zones to obtain increased imaging clarity because a desired frame rate can still be maintained (e.g., since the distance traversed by the multiple ultrasound signals is not so great). However, as imaging depth is increased, maintaining or adding focal zones may have too significant a negative impact on frame rate. As a result, the number of focal zones is decreased. Conversely, in this example, the number of focal zones may be increased if imaging depth is decreased, so as to enhance imaging quality while still maintaining a desired frame rate.

Further example beamformer parameters that may additionally or alternatively be modified at act 420 include the receive filter frequency and/or receive sampling frequency. As noted above with respect to act 415, the frequency of ultrasound signals used to acquire ultrasound images may be adjusted depending on the inputted imaging depth. In various embodiments, as the transmission frequency is being adjusted based on the imaging depth change, the receive frequency may also be adjusted to match the transmission frequency. Additionally or alternatively, the receive sampling frequency can be optimized to match the number of ultrasound samples taken to the vertical pixels in the display area. For example, this may remove potential aliasing and/or enhance optimization of image processing algorithms post beamforming.

Having adjusted frequency and a beamformer parameter at acts 415 and 420, the TGC settings can be adjusted to improve the image being displayed. For example, as shown above in relation to FIG. 3C, using pre-existing TGC settings to acquire an image after modifying frequency and focus position may result in an image that has does not have uniform brightness throughout various imaging depths. Acts 425-435 may thus relate to an automatic TGC adjustment operation.

At 425, the method involves receiving first image data of the ultrasound image feed based on the adjusted frequency and the adjusted beamformer parameter. This first image data may form the baseline image intensity for various regions of the ultrasound image feed 102 (e.g., the baseline image intensity curve) that the adjusted TGC offsets are to be applied.

At 430, based on the first image data, the TGC settings of the ultrasound image feed 102 may be adjusted. The TGC adjustments may be performed with respect to a target image intensity for various regions of the ultrasound image feed 102 (e.g., the target image intensity curve), so that the TGC offsets are applied in a manner so as to substantially achieve the target image intensity curve. In various embodiments, the target intensity curve may be a stored setting for the ultrasound machine set by the ultrasound machine's manufacturer. In some embodiments, the target intensity across multiple imaging depths may be configurable user settings that can be pre-set prior to imaging, so that the TGC adjustments made at act 430 are configured to achieve such inputted target intensities. Such user setting may be considered a general setting that impacts the desired overall brightness of the ultrasound image feed 102.

Act 435 involves receiving second image data of the ultrasound image feed based on the adjusted frequency, beamformer parameter and TGC. Once the TGC offsets for the adjusted frequency and beamformer parameter are determined, additional image data may be received. The TGC offsets can then be applied to this additional data so as to provide the second image data that substantially matches the target intensity curve.

Acts 425-435 above have been described at a high-level, and various additional acts may be performed when performing an automatic TGC operation. In some embodiments, the adjustment of TGC may be performed according to the methods described in U.S. patent application Ser. No. 14/939,993 entitled "Systems and Methods for Automatic Time Gain Compensation in a Handheld Ultrasound Imaging System", the entire contents of which are incorporated herein by reference.

Act 440 involves displaying the second image data on the touchscreen display without receipt of additional user input. By performing acts 415 to 435 in an automated fashion solely upon input received via the single depth control 110' (as shown in FIG. 2), the second image data that reflects these adjustments may appear optimized when displayed.

Figure 5:
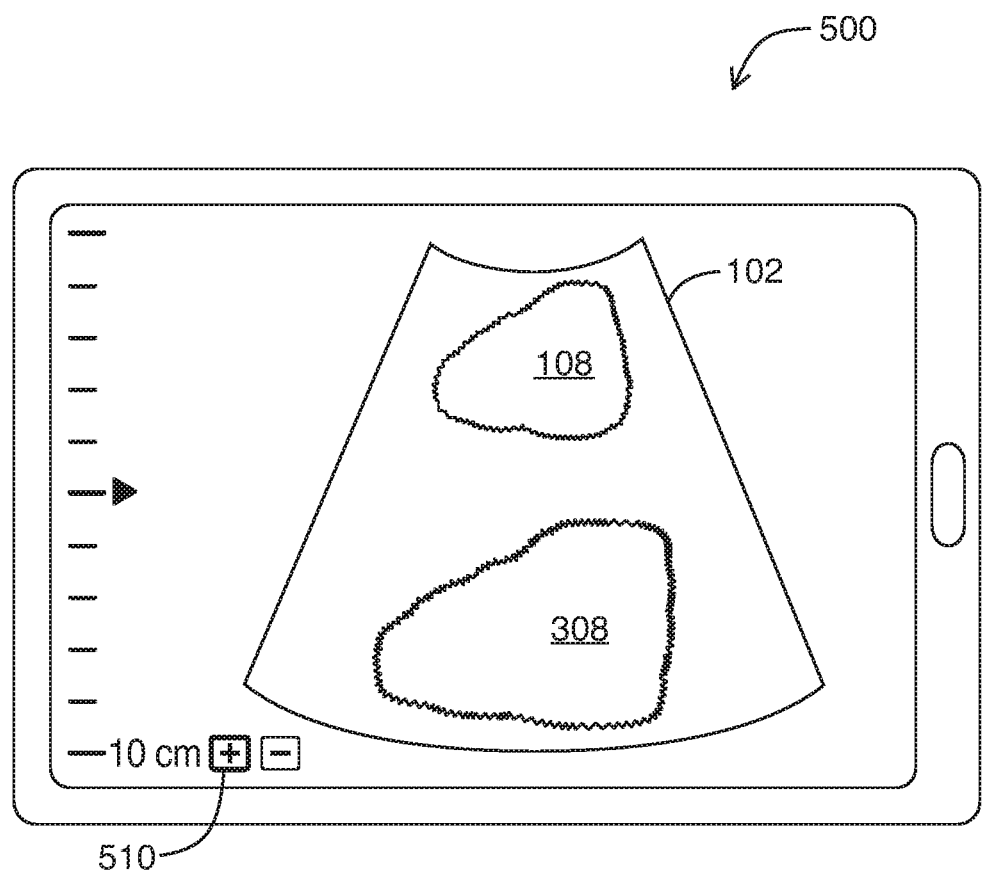
FIG. 5 is an example user interface showing image optimizations resulting from activation of a single user interface control, in accordance with at least one embodiment of the present invention.

Referring to FIG. 5, shown there generally as 500 is an example user interface with image optimizations resulting from activation of a single user interface control, in accordance with at least one embodiment of the present invention. FIG. 5 displays an example user interface that may be shown after activation of the depth control 110' shown in FIG. 2. In the illustrated example, the '+' button 510 (shown with bolded outline) may be selected (e.g., repeatedly pressed or held) to increase the imaging depth to '10 cm'. With the activation of a single control related to imaging depth, it can be seen that the ultrasound image feed 102 can be configured to show both anatomical features 108, 308 within the field of view in a manner that provides substantially similar brightness across various imaging depths. Similar to the anatomical features 108, 308 shown in FIGS. 3B-3D, the anatomical features 108, 308 shown in FIG. 5 is illustrated with jagged lines to indicate the automatically-adjusted lower frequency ultrasound signals used to acquire such images provide increased penetration but lower resolution.

Accordingly, the ultrasound image feed 102 shown in FIG. 5 may provide an image quality that is substantially similar to what is shown in FIG. 3D—but without the requirement of multiple user inputs that is required in traditional systems (as was discussed above with respect to FIGS. 3A-3D). The present embodiments may simplify usability of an ultrasound imaging system. For example, the ability to obtain optimized images based solely on imaging depth may allow ultrasound operators to focus on the tissue they are attempting to image, without being overly concerned about the physics behind acquiring ultrasound images. This user interface may be more intuitive to novice ultrasound users.

In the embodiment shown in FIG. 5, the user interface 500 is also substantially free of a graphical control for modifying any one of: frequency, beamformer parameters (e.g., focus position, number of focal zones), and TGC. This is because a modification of these imaging parameters can be automated based solely on the single imaging depth control, as described above. The reduced number of virtual controls may allow for the ultrasound image feed 102 to occupy more of the screen. This may enhance viewing of the ultrasound image feed 102, especially on smaller screen sizes such as on smartphones which may have screens as small as 3.5" in diagonal length.

In some embodiments, the TGC of the ultrasound image feed 102 may be continuously adjusted after receiving the second image data at act 440 of FIG. 4. This may allow display of subsequent image data from the ultrasound image feed to continually be optimized without receipt of additional user input as aspects of the tissue being imaged changes, for example.

Referring to FIG. 6, shown there generally as 600 is an example preset tree for a curvilinear transducer to be used with a traditional ultrasound imaging system. In traditional ultrasound systems (e.g., such as those discussed above with respect to FIGS. 1, and 3A-3D), a large number of presets are made available to select the type of imaging to be performed. For example, as shown, eighteen (18) presets are made available. The different presets provide pre-configured sets of imaging parameters that are suited for particular types of medical examinations. Due in part to the large number of controls (and thus imaging parameters) that can be adjusted, these presets attempt to provide users with simpler starting points to begin imaging, instead of requiring users to manually adjust the many controls to a point where the best image quality can be obtained for the desired examination type.

Referring to FIG. 7, shown there generally as 700 is an example list of presets for a curvilinear transducer in an ultrasound imaging system of at least one embodiment of the present invention. As shown, the preset list has only five (5) available presets. In contrast with the preset tree shown in FIG. 6, the ultrasound imaging system of the present embodiments can provide a simpler preset list that may be less intimidating to users. Since a number of the imaging parameters can be automatically adjusted based on the input provided via the single imaging depth control, the presets can be configured on a more generic basis that leaves the fine-tuning of parameters traditionally associated with specific presets to be adjusted automatically during imaging.

This may allow the presets of the present embodiments to simply be directed to configuration of settings that are not imaging parameters. For example, the presets may be for making available certain software functionality (e.g., measurement packages) for a given type of medical examination. As shown in FIG. 7, the 'OB/GYN' (obstetrics and gynecology) preset may be configured in a manner substantially similar to the 'Abdomen' preset, except that in the 'OB/GYN' preset, certain 'OB/GYN' measurement packages typically used during such examinations may be made available. In another example, a preset may be for configuring the transducer to behave in a different mode. As shown in FIG. 7, a 'Cardiac' preset may be provided to configure a curvilinear probe to operate in a phased manner using a limited number of available transducer elements (as is described in U.S. patent application Ser. No. 15/207,203 entitled "Methods and Apparatus for Performing Multiple Modes of Ultrasound Imaging using a Single Ultrasound Transducer", the entire contents of which are incorporated herein by reference). Since the presets need not provide default settings for imaging parameters, the preset list can be shorter and thus more accessible and easier to navigate.

Figure 8:
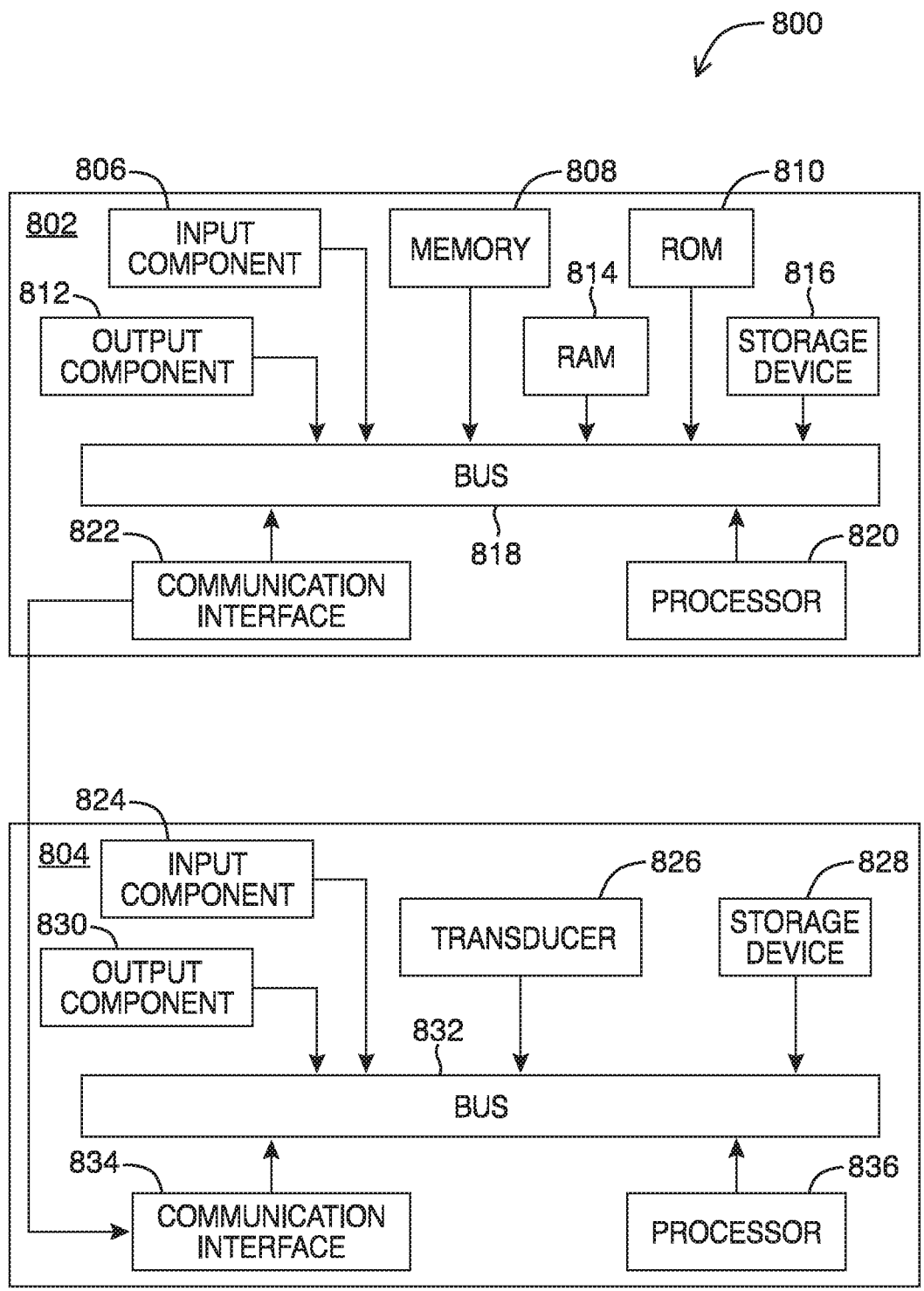
FIG. 8 shows a functional block diagram of an ultrasound system, in accordance with at least one embodiment of the present invention.

Referring to FIG. 8, shown there generally as 800 is a functional block diagram of an ultrasound system, in accordance with at least one embodiment of the present invention. For example, the ultrasound imaging system 800 may be configured to perform the method of FIG. 4, provide the user interfaces shown in FIGS. 2 and 5, and the preset list shown in FIG. 7.

Ultrasound imaging system 800 may include an ultrasound acquisition unit 804 configured to transmit ultrasound energy to a target object, receive ultrasound energy reflected from the target object, and generate ultrasound image data based on the reflected ultrasound energy. The ultrasound acquisition unit 804 may include a transducer 826 which converts electric current into ultrasound energy and vice versa. Transducer 826 may transmit ultrasound energy to the target object which echoes off the tissue. The echoes may be detected by a sensor in transducer 826 and relayed through a bus 832 to a processor 836. Processor 836 may interpret and process the echoes to generate image data of the scanned tissue. In some embodiments, the ultrasound acquisition unit 804 (or various components thereof) may be provided as a handheld ultrasound probe that is in communication with other components of the ultrasound imaging system 800. For example, the handheld probe may include the transducer 826 of ultrasound acquisition unit 804. Ultrasound acquisition unit 804 may also include storage device 828 (coupled to and accessible by bus 832) for storing software or firmware instructions, configuration settings (e.g., sequence tables), and/or ultrasound image data.

Although not illustrated, as will be apparent to one of skill in the art, the ultrasound imaging system 800 may include other components for acquiring, processing and/or displaying ultrasound image data. These include, but are not limited to: a scan generator, transmit beamformer, pulse generator, amplifier, analogue to digital converter (ADC), receive beamformer, signal processor, data compressor, wireless transceiver and/or image processor. Each of these may be components of ultrasound acquisition unit 804 and/or electronic display unit 802 (described below).

Ultrasound imaging system 800 may include an electronic display unit 802 which is in communication with ultrasound acquisition unit 804 via communication interfaces 822/834. In various embodiments, communication interfaces 822/834 may allow for wired or wireless connectivity (e.g., via Wi-Fi™ and/or Bluetooth™) between the electronic display unit 802 and the ultrasound acquisition unit 804. Electronic display unit 802 may work in conjunction with ultrasound acquisition unit 804 to control the operation of ultrasound acquisition unit 804 and display the images acquired by the ultrasound acquisition unit 804. An ultrasound operator may interact with the user interface provided by display unit 802 to send control commands to the ultrasound acquisition unit 804 to adjust single control discussed herein. The electronic display unit 802 may be a portable device, which may include a mobile device (e.g. smartphone), tablet, laptop, or other suitable device incorporating a display and a processor and capable of accepting input from a user and processing and relaying the input to control the operation of the ultrasound acquisition unit 804 as described herein.

Each of ultrasound acquisition unit 804 and display unit 802 may have one or more input components 824, 806 and/or one or more output components 830, 812. In the FIG. 8 embodiment, ultrasound acquisition unit 804 may include an input component 824 which is configured to accept input from the user (e.g., to turn on the ultrasound acquisition unit 804 or control the connection of the ultrasound acquisition unit 804 to the electronic display unit 802). For example, in some embodiments, ultrasound acquisition unit 804 may also include an output component 830, such as a LED indicator light which can output the status of the ultrasound acquisition unit 804.

In the FIG. 8 embodiment, display unit 802 may include an input component 806 configured to accept input from the user. Certain input received at input component 806 may be relayed to ultrasound acquisition unit 804 to control the operation of ultrasound acquisition unit 804. Display unit 802 may also include an output component 812, such as a display screen, which displays images based on image data acquired by ultrasound acquisition unit 804. In particular embodiments, display unit 802's input component 806 may include a touch interface layered on top of the display screen of the output component 812. Electronic display unit 802 may also include memory 808, Random Access Memory (RAM) 814, Read Only Memory (ROM) 810, and persistent storage device 816, which may all be connected to bus 818 to allow for communication therebetween and with processor 820. Ultrasound acquisition unit 804 may contain memory (e.g., storage device 828) that may be accessible by processor 836. Any number of these memory elements may store software or firmware that may be accessed and executed by processor 820 and/or processor 836 to, in part or in whole, perform the acts of the methods described herein (e.g., so that the processor 820 is configured to provide the user interfaces of FIGS. 2 and 5 discussed herein on display unit 802).

In some embodiments, all of the input controls and display screen necessary for the operation of the ultrasound imaging system 800 may be provided by input and output components 806, 812 of the display unit 802. In such cases input and output components 824, 830 of ultrasound acquisition unit 804 may be optional and/or omitted. In certain embodiments, the ultrasound acquisition unit 804 may be a handheld probe (i.e. including transducer 826) which is in communication with the display unit 802 over the communications interfaces 822/834 to facilitate operation of the ultrasound acquisition unit 804 and processing and display of ultrasound images.

In various embodiments, at least a portion of the processing of the image data corresponding to the reflected ultrasound energy detected by the handheld probe's transducer 826 may be performed by one or more of processors internal to the ultrasound acquisition unit 804 (such as by the processor 836) and/or by processors external to the ultrasound acquisition unit 804 (such as the processor 820 of electronic display unit 802). By having some of the image data processing tasks typically performed by a processor 836 of ultrasound acquisition unit 804 be performed instead by a processor 820 of the display unit 802, less physical processing hardware may need to be provided on the ultrasound acquisition unit 804. This may facilitate a lightweight, portable design and construction for the ultrasound acquisition unit 804 (e.g., when it is a handheld probe). In particular embodiments the handheld probe may have a mass that is less than approximately 1 kg (2 lbs).

In some embodiments, the output component 830 of ultrasound acquisition unit 804 may include a display screen, which can be configured to display or otherwise output the images acquired by ultrasound acquisition unit 804 (in addition to or alternative to displaying such images on the display unit 802).

As noted, the ultrasound imaging system 800 of FIG. 8 may be configured to perform the method of FIG. 4, so as to receive the touch input and display the user interfaces in FIGS. 2 and 5. The discussion below will be made with simultaneous reference to FIGS. 2 and 5, and the components of FIG. 8, to illustrate how such components may be involved in performing various acts of the method of FIG. 4. Steps of method 400 in FIG. 4 may be implemented as software or firmware contained in a program memory 808, 814, 810 or storage device 816 accessible to a processor 820 of display unit 802 and/or a storage device 828 accessible to processor 836 of ultrasound acquisition unit 804. Processor 820/836 may independently or collectively implement various acts of method 400 of FIG. 4 by executing software instructions provided by the software.

For example, when doing so, the initial imaging parameters shown in the live ultrasound image feed may be defined by the current or initial imaging parameters of ultrasound acquisition unit 804 and/or electronic display unit 802. The current or initial imaging parameters may have been pre-loaded to the electronic display unit 802 (e.g. from manufacturer's settings) based on the initial imaging depth.

Ultrasound image data may be obtained, for example, by ultrasound acquisition unit 804 employing a high frequency, high voltage pulse to excite transducer 826 to emit ultrasound waves and receiving the reflected ultrasound waves. In particular embodiments, the ultrasound acquisition unit 804 may be a probe which acquires ultrasound image data by generating pulses of a specified amplitude in accordance with an ultrasound sequence specified in a sequence table. The probe may perform ultrasound beam generation using transmit beamforming, detects and receives the ultrasound echo and performs receive beamforming, and processes the data based on the sequence specified in the sequence table. The probe may transmit the processed ultrasound image data to a display unit 802 which has a processor 820 that further processes the data for display (e.g. scan conversion) and then displays the ultrasound image on the output component (e.g., screen) 812.

Scan conversion may then be performed on the data to transform the image data in a manner that allows it to be displayed in a form that is more suitable for human visual consumption. For example, this may involve converting the image data from the data space (e.g. polar coordinate form) to the display space (e.g. Cartesian coordinate form). The acquired ultrasound images may be displayed on the output component 812 of display unit 802 (act 405 of FIG. 4). Scan conversion is one of the actions that renders the image data suitable for display. However, as will be apparent to those of skill in the art, other technological steps may also need to be performed, such as, for example, amplification and/or digitization of the data. After the scan conversion, an ultrasound image may be displayed by the electronic display unit 802.

If an ultrasound operator wishes to modify the imaging depth parameter, they may input a touchscreen command to direct the ultrasound imaging system 100 via the single control provided on the touchscreen of the electronic display unit 802 (act 410 of FIG. 4). For example, the input component 806 of display unit 802 may include a touch interface that detects the user input and interprets the command based on the user input being received. The touchscreen interface may receive the input and provide it to processor 820 which executes software instructions to analyse the input and determine the command associated with the input.

Upon input via the single imaging depth control, the display unit 102 may transmit the command to modify imaging depth to the ultrasound acquisition unit 804 via communication interfaces 822, 834. In turn, the ultrasound acquisition unit 804 may adjust various imaging parameters such as frequency and beamformer parameters used by the transducer 826 to acquire ultrasound image data (acts 415-420 of FIG. 4). Then, new image data may be acquired and a TGC operation performed on the new image data at either the display unit 802 and/or the ultrasound acquisition unit 804 (acts 425-435 of FIG. 4). These operations may help optimize visualization of the acquired image data. The optimized image data may then be displayed on the output component 812 (e.g., a touchscreen display) of the electronic display unit 802 (act 440 of FIG. 4).

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

INTERPRETATION OF TERMS

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the coupling or connection between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms.

Unless the context clearly requires otherwise, throughout the description and the claims:
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An ultrasound imaging system, comprising:
a touchscreen display; and
a processor configured to execute instructions that cause the processor to provide a user interface on the touchscreen display, the user interface comprising a live ultrasound image feed being acquired by the ultrasound imaging system, wherein the user interface further comprises a single control for modifying imaging depth of the live ultrasound image feed being acquired by the ultrasound imaging system, and the user interface is free of graphical controls for modifying non-depth imaging parameters of the live ultrasound image feed being acquired by the ultrasound imaging system;
wherein upon receipt of input via the single control to modify the imaging depth of the live ultrasound image feed, the processor, prior to displaying a subsequent frame of the live ultrasound image feed, causes the ultrasound imaging system to:
adjust frequency of ultrasound signals to be used to acquire the subsequent frame of the live ultrasound image feed,
adjust a beamformer parameter of the ultrasound signals to be used to acquire the subsequent frame of the live ultrasound image feed,
acquire first image data based on the adjusted frequency and the adjusted beamformer parameter,
based on the first image data, adjust Time Gain Compensation (TGC) to be used to acquire the subsequent frame of the live ultrasound image feed, and
acquire second image data based on the adjusted frequency, beamformer parameter and TGC;
so that the second image data is used as the subsequent frame of the live ultrasound image feed and displayed on the touchscreen display, without receipt of additional user input other than the input received via the single control to modify the imaging depth of the live ultrasound image feed.

2. The ultrasound imaging system of claim 1, wherein the input for the single control is receivable via a touch gesture on the touchscreen display.

3. The ultrasound imaging system of claim 2, wherein the touch gesture comprises a drag gesture.

4. The ultrasound imaging system of claim 1, wherein the graphical controls that the user interface is free of includes: frequency, focus position, number of focal zones, and TGC.

5. The ultrasound imaging system of claim 1, wherein the beamformer parameter comprises one of: focus position, number of focal zones, receive filter frequency, or receive sampling frequency.

6. The ultrasound imaging system of claim 1, wherein TGC of the live ultrasound image feed is continuously adjusted after receiving the second image data, so that subsequently acquired image data of the live ultrasound image feed is optimized for display without receipt of additional user input.

7. The ultrasound imaging system of claim 1, wherein adjusting the TGC to be used to acquire the subsequent frame of the live ultrasound image feed comprises determining TGC offsets across multiple imaging depths of the first image data.

8. The ultrasound imaging system of claim 7, wherein the TGC offsets are for achieving a predetermined target image intensity across the multiple imaging depths.

9. A method of controlling viewing of a live ultrasound image feed being acquired by an ultrasound imaging system, the method comprising:
providing a user interface on a touchscreen display, the user interface comprising the live ultrasound image feed being acquired by the ultrasound imaging system, wherein the user interface further comprises a single control for modifying imaging depth of the live ultrasound image feed being acquired by the ultrasound imaging system, and the user interface is free of graphical controls for modifying non-depth imaging parameters of the live ultrasound image feed being acquired by the ultrasound imaging system;
receiving input via the single control to modify the imaging depth of the live ultrasound image feed;
upon receipt of the input, prior to displaying a subsequent frame of the live ultrasound image feed,
adjusting frequency of ultrasound signals to be used to acquire the subsequent frame of the live ultrasound image feed,
adjusting a beamformer parameter of the ultrasound signals to be used to acquire the subsequent frame of the live ultrasound image feed,
acquiring first image data based on the adjusted frequency and the adjusted beamformer parameter,
based on the first image data, adjusting Time Gain Compensation (TGC) to be used to acquire the subsequent frame of the live ultrasound image feed, and
acquiring second image data based on the adjusted frequency, beamformer parameter and TGC;
so that the second image data is used as the subsequent frame of the live ultrasound image feed and displayed on the touchscreen display, without receipt of additional user input other than the input received via the single control to modify the imaging depth of the live ultrasound image feed.

10. The method of claim 9, wherein the input for the single control is received via a touch gesture on the touchscreen display.

11. The method of claim 10, wherein the touch gesture comprises a drag gesture.

12. The method of claim 9, wherein the graphical controls that the user interface is free of includes: frequency, focus position, number of focal zones, or TGC.

13. The method of claim 9, wherein the beamformer parameter comprises one of: focus position, number of focal zones, receive filter frequency, or receive sampling frequency.

14. The method of claim 9, wherein TGC of the live ultrasound image feed is continuously adjusted after receiving the second image data, so that subsequently acquired image data of the live ultrasound image feed is optimized for display without receipt of additional user input.

15. The method of claim 9, wherein adjusting the TGC to be used to acquire the subsequent frame of the live ultrasound image feed comprises determining TGC offsets across multiple imaging depths of the first image data.

16. The method of claim 15, wherein the TGC offsets are for achieving a predetermined target image intensity across the multiple imaging depths.

17. A computer readable medium storing instructions for execution by a processor of a display unit for an ultrasound imaging system, the display unit having a touchscreen display, wherein when the instructions are executed by the processor, the display unit is configured to:
provide a user interface on the touchscreen display, the user interface comprising a live ultrasound image feed being acquired by the ultrasound imaging system, wherein the user interface further comprises a single control for modifying imaging depth of the live ultrasound image feed being acquired by the ultrasound imaging system, and the user interface is free of graphical controls for modifying non-depth imaging parameters of the live ultrasound image feed being acquired by the ultrasound imaging system; and
receive input via the single control to modify the imaging depth of the live ultrasound image feed;
wherein upon receipt of the input, the processor, prior to displaying a subsequent frame of the live ultrasound image feed, causes the ultrasound imaging system to:
adjust frequency of ultrasound signals to be used to acquire the subsequent frame of the live ultrasound image feed,
adjust a beamformer parameter of the ultrasound signals to be used to acquire the subsequent frame of the live ultrasound image feed,
acquire first image data based on the adjusted frequency and the adjusted beamformer parameter,
based on the first image data, adjust Time Gain Compensation (TGC) to be used to acquire the subsequent frame of the live ultrasound image feed, and
acquire second image data based on the adjusted frequency, beamformer parameter and TGC;
so that the second image data is used as the subsequent frame of the live ultrasound image feed and displayed on the touchscreen display, without receipt of additional user input other than the input received via the single control to modify the imaging depth of the live ultrasound image feed.

18. The computer readable medium of claim 17, wherein the graphical controls that the user interface is free of include: frequency, focus position, number of focal zones, or TGC.

19. The computer readable medium of claim 17, wherein the beamformer parameter comprises one of: focus position, number of focal zones, receive filter frequency, or receive sampling frequency.

* * * * *